(12) United States Patent
Chandrapati et al.

(10) Patent No.: US 11,319,573 B2
(45) Date of Patent: May 3, 2022

(54) **RAPID DETECTION OF *E. COLI* IN A THIN FILM CULTURE DEVICE**

(71) Applicant: 3M INNOVATIVE PROPERTIES COMPANY, St. Paul, MN (US)

(72) Inventors: Sailaja Chandrapati, Woodbury, MN (US); Alec J. Teagarden, Savage, MN (US); Haley A. Saddoris, Minneapolis, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 275 days.

(21) Appl. No.: 16/492,715

(22) PCT Filed: Apr. 2, 2018

(86) PCT No.: PCT/US2018/025641
§ 371 (c)(1),
(2) Date: Sep. 10, 2019

(87) PCT Pub. No.: WO2018/187197
PCT Pub. Date: Oct. 11, 2018

(65) Prior Publication Data
US 2020/0109431 A1   Apr. 9, 2020

Related U.S. Application Data

(60) Provisional application No. 62/480,633, filed on Apr. 3, 2017.

(51) Int. Cl.
*C12Q 1/06* (2006.01)
*C12M 1/00* (2006.01)
(Continued)

(52) U.S. Cl.
CPC ............... *C12Q 1/06* (2013.01); *C12M 29/04* (2013.01); *C12M 33/02* (2013.01); *C12M 41/36* (2013.01);
(Continued)

(58) Field of Classification Search
CPC ... C12Q 1/06; C12Q 1/40; C12Q 1/10; C12Q 2334/52; C12Q 2304/24; C12Q 2304/46; C12M 29/04; C12M 33/02; C12M 41/36
See application file for complete search history.

(56) References Cited

U.S. PATENT DOCUMENTS

| 4,565,783 A | 1/1986 | Hansen |
| 5,089,413 A | 2/1992 | Nelson |

(Continued)

FOREIGN PATENT DOCUMENTS

| JP | 2001-333795 A | 12/2001 |
| JP | 2008-17712 A | 1/2008 |

(Continued)

OTHER PUBLICATIONS

US 4,476,226 A, 10/1984, Hansen (withdrawn)
(Continued)

*Primary Examiner* — Sean C. Barron
(74) *Attorney, Agent, or Firm* — 3M IPC

(57) ABSTRACT

A device for differentially enumerating colonies of coliform and *Escherichia coli* microorganisms is provided. The device comprises a water-impermeable first sheet; a water-impermeable second sheet attached to the first sheet; a dry, rehydratable culture medium comprising a lactose-fermentation indicator system, a β-D-glucuronidase indicator system that comprises a plurality of compounds that enhance β-glucuronidase enzyme activity in *E. coli*, a redox indicator system and a first cold-water soluble gelling agent adhered to the first sheet, the culture medium disposed in a microbial (Continued)

growth zone; and a second cold-water-soluble gelling agent adhered to the second sheet. The microbial growth zone is disposed between the first sheet and the second sheet. Methods of using the device are also provided.

20 Claims, 1 Drawing Sheet

(51) Int. Cl.
    C12M 1/30      (2006.01)
    C12M 1/34      (2006.01)
    C12Q 1/10      (2006.01)
    C12Q 1/40      (2006.01)
(52) U.S. Cl.
    CPC ............... C12Q 1/10 (2013.01); C12Q 1/40
        (2013.01); C12Q 2304/24 (2013.01); C12Q
        2304/46 (2013.01); C12Q 2334/52 (2013.01)

(56) References Cited

U.S. PATENT DOCUMENTS

| | | | |
|---|---|---|---|
| 5,137,812 | A | 8/1992 | Matner |
| 5,210,022 | A | 5/1993 | Roth |
| 5,364,766 | A * | 11/1994 | Mach ............... C12N 1/20 422/552 |
| 5,384,766 | A | 1/1995 | Yamato |
| 5,510,243 | A | 4/1996 | Boyd |
| 5,518,895 | A * | 5/1996 | Thorpe ............. C12M 41/26 435/287.5 |
| 5,601,998 | A | 2/1997 | Mach |
| 5,605,812 | A | 2/1997 | Zomer |
| 5,723,308 | A | 3/1998 | Mach |
| 5,795,773 | A * | 8/1998 | Read ............... C12M 29/20 435/287.5 |
| 5,861,270 | A | 1/1999 | Nelis et al. |
| 6,090,541 | A | 7/2000 | Wicks |
| 6,632,661 | B2 | 10/2003 | Wickert |
| 6,641,996 | B1 * | 11/2003 | Jefferson ........... C12N 9/2402 435/6.13 |
| 2010/0255530 | A1 | 10/2010 | Monget et al. |
| 2013/0273598 | A1 * | 10/2013 | Moriyama ........... C12Q 1/44 435/38 |

FOREIGN PATENT DOCUMENTS

| WO | WO 95/03424 A | 2/1995 | |
|---|---|---|---|
| WO | WO-2012092090 A1 * | 7/2012 | ............ A61P 1/06 |
| WO | WO 2018-187195 | 10/2018 | |

OTHER PUBLICATIONS

Ferraz et al. Evaluation of Enterobacteriaceae in the powdered milk production chain using both traditional (ISO 21528:2) and rapid (3M™ Petrifilm™) methods. Ann Microbiol (2010), 60, 373-376. (Year: 2010).*
"Petrifilm™ E.coli/Coliform Count Plates", retrieved from the Internet on Dec. 6, 2005, URL <http://f1le.southernbiological.com/Assets/Products/Kits_and_Equipment/Petrifilm/Count_Plates/M6404-Petn film E coli Coliform/EcoliColiformCountInsert.pdf>, 2005, pp. 1-2, XP055481370.
Delisle, "Rapid Detection of Escherichia coli in Urine Samples by a New Chromogenic β-Glucuronidase Assay", Journal of Clinical Microbiology, 1989, vol. 27, No. 04, pp. 778-779.
Fricker, "False-Negative B-D-Glucuronidase Reactions in Membrane Lactose Glucuronide Agar Medium Used for the Simultaneous Detection of Coliforms and Escherichia coli From Water", Letters in Applied Microbiology, 2008, vol. 47, No. 06, pp. 539-542.
George, "Use of Enzymatic Methods for Rapid Enumeration of Coliforms in Freshwaters", Journal of Applied Microbiology, 2000, vol. 88, No. 03, pp. 404-413, XP002782115.
Millipore Sigma, "Lactose TTC Agar with Tergitol® 7", Merck Microbiology Manual 12th Edition, retrieved from the internet on Jun. 5, 2005, URL < http://www.emdmillipore.com/us/en/product/msds/MDA_CHEM-107680?Origin=PDP>, 2005, p. 1, XP055481333.
Novel, "Inducibility of β-Glucurnidase in Wild-Type and Hexuronate-Negative Mutants of Escherichia coli K-12", Journal of Bacteriology, 1974, vol. 120, No. 01, pp. 89-95.
Oya, "Studies on Microbial Utilization of D-Glucuronic Acid Derivatives", Journal of Microbiology, 1960, vol. 04, No. 03, pp. 317-326.
Park, "Evaluation of Dry Medium (Sanita-Kun) for Enumeration of Coliforms and Escherichia coli in Milk, Ice Cream, Ham, and Codfish Fillet", Food Science and Biotechnology, 2012, vol. 21, No. 06, pp. 1789-1793, XP055481385.
Poucke, "Rapid Detection of Fluorescent and Chemiluminescent Total Coli Forms and Escherichia coli on Membrane Filters", Journal of Microbiological Methods, 2000, vol. 42, No. 03, pp. 233-244, XP002782114.
Tryland, "Enzyme Characteristics of β-D-Galactosidase- and β-D-Glucuronidase-Positive Bacteria and Their Interference in Rapid Methods for Detection of Waterborne Coliforms and Escherichia coli", Applied and Environmental Microbiology, 1998, vol. 64, No. 03, pp. 1018-1023.
International Search Report for PCT International Application No. PCT/US2018/025641, dated Jun. 19, 2018, 5 pages.

* cited by examiner

RAPID DETECTION OF *E. COLI* IN A THIN FILM CULTURE DEVICE

CROSS-REFERENCE TO RELATED APPLICATIONS

This application is a national stage filing under 35 U.S.C. 371 of PCT/US2018/025641, filed Apr. 2, 2018, which claims the benefit of U.S. Provisional Application No. 62/480,633, filed Apr. 3, 2017, the disclosure of which is incorporated by reference in its/their entirety herein.

BACKGROUND

In food and beverage safety testing, the presence or absence of coliform bacteria is considered to be important evidence of quality. The amount of coliform bacteria permitted in beverages and in certain foods (for example, dairy products) is regulated in many countries around the world. Coliform bacteria include fecal coliforms, such as *Escherichia coli*. The presence of fecal coliforms in a food or water sample is used as a primary indicator of fecal contamination of the food or water and of the possible presence of other pathogenic microorganisms.

Methods for detecting, identifying, and/or enumerating microorganisms in food samples often vary according to the nature of the food and the types of microorganisms that are likely to be found in the samples. Compendia of methods for testing food samples include Standard Methods for the Examination of Dairy Products, 27.sup.th Edition, published by The American Public Health Association, Washington, D.C., and the Bacteriological Analytical Manual ("BAM"), published by the U.S. Food and Drug Administration, Washington, D.C. Solid foods are usually suspended in aqueous media and mixed and/or pulverized to obtain a liquid homogenate of the food material, which can be used in methods of quantitative microbial analysis.

The above-referenced methods, however, are generally relatively expensive, involve multiple steps, require about 24- to 48-hour incubation periods before colonies can be counted, and/or require relatively sophisticated instrumentation and/or relatively highly trained personnel.

There is a need for faster methods for enumerating viable coliform and *E. coli* microorganisms in food and beverage samples.

SUMMARY

In general, the present disclosure relates to detection and optional enumeration of microorganisms in a sample. In particular, the present disclosure relates to culture devices that can be used to grow colony-forming units (CFUs) of coliform bacteria in a semi-solid culture medium and to differentially enumerate coliform CFUs and *E. coli* CFUs. The inventive culture device includes a plurality of compounds that enhance β-glucuronidase activity in *E. coli* and is particularly useful for detecting and differentiating colonies of β-glucuronidase-positive *E. coli* I, for example constitutive and inducible β-glucuronidase-positive *E. coli*, thereby providing more-accurate counts of the microorganisms present in a sample. The culture medium typically contains TTC, which can enable differentiation and visualization of non-beta glucuronidase producing coliform bacteria. In addition, the culture medium used in the device typically provides faster detection and enumeration of coliform bacteria and *E. coli* than prior thin-film culture devices The present disclosure also provides methods of using the culture devices. The inventive methods disclosed herein provide for growth, detection, and differentiation of coliform and *E. coli* bacteria. The methods permit faster and more-accurate enumeration of coliform and *E. coli* colonies at multiple temperatures (e.g. 35-37 and 42-44 C) than prior methods that used thin-film culture devices for enumerating coliform and *E. coli* colonies. In one aspect, the present disclosure provides a device for differentially enumerating colonies of coliform and *Escherichia coli* microorganisms. The device can comprise a water-impermeable first sheet; a water-impermeable second sheet attached to the first sheet; a dry, rehydratable culture medium comprising a first cold-water soluble gelling agent adhered to the first sheet; a microbial growth zone disposed between the first sheet and the second sheet; and a second cold-water-soluble gelling agent adhered to the second sheet. The culture medium can comprise organonitrogenous nutrients that facilitate growth of coliform microorganisms, a lactose-fermentation indicator system, a β-D-glucuronidase indicator system, tetrazolium chloride indicator and an effective amount of at least one agent that selectively inhibits growth of non-coliform microorganisms. An area of the culture medium adhered to the first sheet defines the growth zone. The lactose-fermentation indicator system comprises D-lactose, a first inducer compound that enhances production of β-galactosidase, and a pH indicator. The β-D-glucuronidase indicator system comprises 5-bromo-4-chloro-3-indolyl-β-D-glucuronide and a plurality of compounds that enhance β-glucuronidase enzyme activity in *E. coli*. The first sheet is attached to the second sheet so that the culture medium is facing the second cold-water-soluble gelling agent. The first sheet and second sheet are configured to retard passage of carbon dioxide therethrough.

In any of the above embodiments, at least one of the plurality of compounds that enhance β-glucuronidase enzyme activity in *E. coli* is D-glucuronic acid. In any of the above embodiments, the first sheet and/or the second sheet can comprise a polyester film. In any of the above embodiments, the second sheet can comprise polyethylene terephthalate. In any of the above embodiments, the growth zone can be defined by a spacer adhered to the first sheet. In any of the above embodiments, the culture medium further comprises a reagent for buffering the culture medium, when reconstituted with an aqueous liquid, at a pH between about 6.5 and about 8. In any of the above embodiments, the organonitrogenous nutrients are selected from a group consisting of yeast extract, porcine peptones, an enzymatic digest of gelatin, an enzymatic digest of animal peptone, and a combination of any two or more of the foregoing organonitrogenous nutrients. In any of the above embodiments, the agent can be selected from a group consisting of bile salts, sodium dodecyl sulfate, and combinations thereof.

In another aspect, the present disclosure provides a method of differentially enumerating colonies of coliform and *Escherichia coli* microorganisms via TTC reduction and constitutive and inducible beta glucuronidase expression respectively.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a nutrient can be interpreted to mean "one or more" nutrients.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

The invention may be further illustrated by reference to the accompanying drawings wherein.

Figure 1:
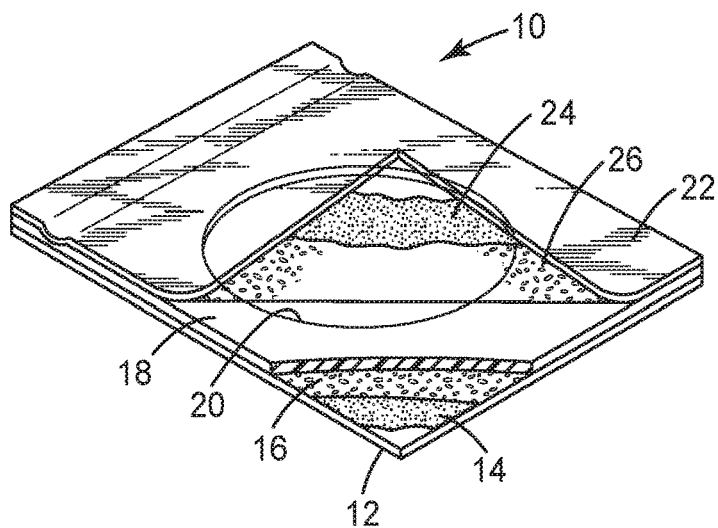
FIG. 1 is a top perspective view, partially in section, of a preferred microbiological growing device of the present disclosure.

While the above-identified drawing figures set forth several embodiments of the disclosure, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The term "culture" or "growth" of microorganisms as used herein refers to the method of multiplying microbial organisms by letting them reproduce in predetermined culture media under conditions conducive for their growth. More particularly it is the method of providing a suitable culture medium and conditions to facilitate at least one cell division of a microorganism. Culture media are solid, semi-solid or liquid media containing all of the nutrients and necessary physical growth parameters necessary for microbial growth.

The term "enrichment" as used herein refers to the culture method of selectively enriching the growth of a specific microorganism by providing medium and conditions with specific and known attributes that favors the growth of that particular microorganism. The enrichment culture's environment will positively influence the growth of a selected microorganism and/or negatively influence the growth of other microorganisms.

The present disclosure generally relates to methods for growing and detecting and differentially enumerating coliform and *E. coli* colonies in a thin film culture device that contains a cold water-soluble gelling agent.

"Coliform bacteria" collectively refers to a group of several genera (e.g., *Citrobacter, Enterobacter, Hafnia, Klebsiella, Serratia* and *Escherichia*) of bacteria that have the ability to ferment lactose with a resultant production of acid and gas. Most coliform bacteria are generally considered nonpathogenic to humans. However, some coliform bacteria (e.g., *Escherichia coli*) include strains that are highly pathogenic. Coliforms are found in the fecal matter of mammals and are commonly used as an indicator of fecal contamination of food and/or water.

Suitable sample materials can be obtained or derived from a variety of sources. The term "source" is generally used to refer to the food or nonfood desired to be tested for microorganisms. The source can be a solid, a liquid, a semi-solid, a gelatinous material, gas (e.g., air), and combinations thereof. In some embodiments, the source can be provided by a capture element that was used, for example, to collect the source from a surface of interest or from air. In some embodiments, the liquid composition can include the capture element, which can be further broken apart (e.g., during an agitation or dissolution process) to enhance retrieval of the source and any microorganism of interest. The surface of interest can include at least a portion of a variety of surfaces, including, but not limited to, walls (including doors), floors, ceilings, drains, refrigeration systems, ducts (e.g., air ducts), vents, toilet seats, handles, doorknobs, handrails, countertops, tabletops, eating surfaces (e.g., trays, dishes, etc.), working surfaces, equipment surfaces, clothing, etc., and combinations thereof. All or a portion of the source can be used in the method. When a portion of the source is used, this can sometimes be referred to as a "sample" of the source. However, the term "sample" is generally used herein to refer to the portion of volume or mass of material that is obtained from the source and is introduced into a test device for the detection of microorganisms.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, beer, animal feed, other suitable comestible materials, and combinations thereof.

The term "TTC" is an abbreviation for the dye triphenyl tetrazolium chloride.

One type of thin film culture devices known in the art, comprising two adjoined sheets with dry culture medium adhered therebetween, is described in U.S. Pat. No. 4,565,783. These devices are useful for growing, detecting, and enumerating a variety of microorganisms including, for example, total aerobic bacteria or coliform bacteria.

Figure 2:
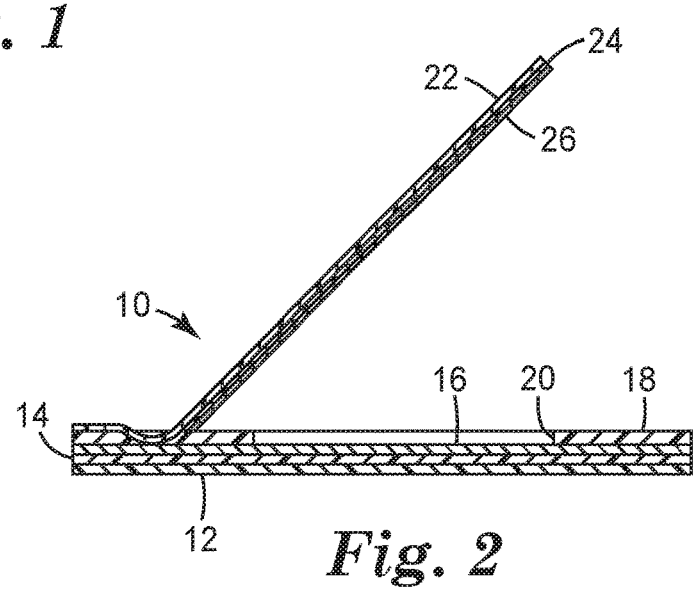
FIG. 2 is a cross sectional view of device of FIG. 1.
Figure 3:
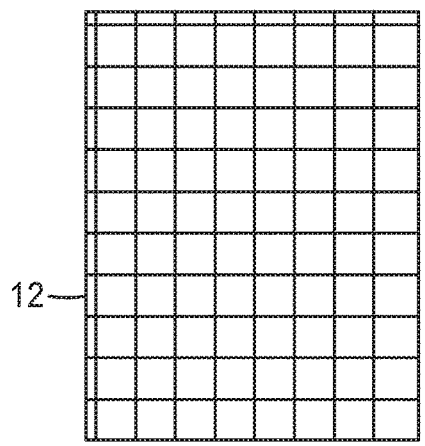
FIG. 3 is a top view of a grid pattern that can be printed on the first sheet or the second sheet of the device of FIG. 1.

In one aspect, the present disclosure provides a device. FIGS. 1 and 2 illustrate one embodiment of a device in accordance with the present disclosure. The microbiological growing device 10 includes a body member comprising a self-supporting water-proof first sheet 12 having upper and lower surfaces. The first sheet 12 is preferably a relatively stiff film of a material such as polyester, polypropylene or polystyrene which will not absorb or otherwise be affected by water. Polyester films approximately 0.1 mm to 0.18 mm thick, polypropylene films approximately 0.1 mm to 0.2 mm thick and polystyrene films approximately 0.38 mm thick have been found to work well. Other suitable first sheets include photoprint paper with a polyethylene or other water-proof coating, as described in U.S. Pat. No. 4,565,783. The first sheet 12 may be either transparent or opaque, depending on whether one wishes to view bacterial colonies through the first sheet. To facilitate the counting of bacterial colonies, the first sheet 12 may have a pattern (e.g., a square grid pattern) printed thereon as shown in FIG. 3.

Adhered to the first sheet 12 is a culture medium 16 that comprises a first cold-water-soluble gelling agent described herein. Also adhered (either directly or indirectly) to the first sheet 12 of the device 10 is a second sheet 22. Second sheet 22 is preferably transparent to facilitate counting of the bacterial colonies in the device and is substantially impermeable to bacteria and water vapor. As used in the specification and claims, "substantially impermeable to bacteria and moisture vapor" designates second sheets which prevent undesired contamination (e.g., microbial contamination) of the dehydrated medium during shipping, storage and use of the devices and which provide an environment that will support growth of microorganisms during the incubation period.

Generally, the second sheet 22 will have properties similar to first sheet 12, but need not be as stiff. Suitable materials for the second sheet 22 include plastic films such as, for example, polypropylene (e.g., 40 μm-thick biaxially-oriented polypropylene (BOPP)) and polyester (e.g., polyethylene terephthalate (PET) that is about 70 μm thick). The density of PET (e.g., about 1.38 g/mm$^3$) is often higher than the density of BOPP (e.g., about 0.92 g/mm$^3$). Optionally, the first sheet 12 and second sheet 22 are configured to retard passage of carbon dioxide therethrough. Advantageously, a device constructed with first and second sheets that are configured to retard passage of carbon dioxide therethrough is more effective at trapping biogenic carbon dioxide (e.g., carbon dioxide produced by the fermentation of a carbohydrate) adjacent a colony in the device that has produced the biogenic carbon dioxide (e.g., by the fermentation of lactose present in the device).

The first sheet 12 optionally is coated on one of its major surfaces with a layer of an adhesive 14 which serves to hold a dry, rehydratable culture medium 16 on the first sheet in a uniform monolayer for easy hydration. Alternatively, adhesive 14 can be coated onto second sheet 22 and the culture medium coated onto first sheet 12. In either event, adhesive 14 and adhesive 24 preferably are water-insoluble and non-inhibitory to the growth of microorganisms. Preferably, the adhesives are sufficiently transparent when wet to enable the viewing of bacterial colonies through the film coated with the adhesive. Suitable adhesives for use in adhesive 14 and adhesive 24 include, for example, pressure-sensitive adhesives. However, heat-activated adhesives wherein a lower melting substance is coated onto a higher melting substance may also be used. Water-activated adhesives such as mucilage may also be useful. Adhesive 14 preferably contains TTC, although other additives or dyes are occasionally used. Unlike in some previously reported cases, the culture devices and methods described herein do not require the addition of pyruvic acid or pyruvates. In many preferred cases, the culture devices described herein, as well as the methods in which they are used, are free of pyruvic acid and its salts. Adhesive 14 (usually containing TTC) should be coated onto first sheet 12 or second sheet 22, as the case may be, in a thickness which does not substantially interfere with or prevent observation (e.g., manual or mechanical observation) of microbial colonies growing in the device and/or does not substantially interfere with or prevent transmission of electromagnetic radiation (e.g., visible light) that is used to observe the microbial colonies. Typically, when adhesive 14 is coated onto first sheet 12, it is followed by a second coating of cell culture medium. A non-limiting example of an adhesive suitable for use in a device of the present disclosure is a copolymer of isooctylacrylate/acrylamide (in a mole ratio of 94/6). Other pressure sensitive adhesives which may be used include isooctylacrylate/acrylic acid (in a mole ratio of 95/5 or 94/6) and silicone rubber. Adhesives which turn milky upon exposure to water are less preferred, but may be used in conjunction with a nontransparent first sheet or where colony visualization is not required.

Coated onto at least a portion of the optional adhesive 14 (usually containing TTC and/or directly onto the first sheet 12 is a coating comprising a dry, rehydratable culture medium 16. The dry culture medium 16 is substantially water-free. As used in the specification and claims, the phrase "substantially water-free" designates a coating which has a water content no greater than about the water content of the dehydrated coating once it has been permitted to equilibrate with the ambient environment. A uniform monolayer of dry culture medium 16 is desired to ensure uniformity of the rehydrated culture media. The dry, rehydratable culture medium should have sufficient surface area exposed in a microbial growth zone for hydration during use. Generally, an adhesive layer in the thickness range of about 5 μm to about 13 μm is suitable.

As an alternative to the illustrative embodiment of FIGS. 1 and 2, it is contemplated that a device of the present disclosure can comprise a pedestal with the culture medium disposed thereon and can be assembled in a manner similar to the culture device disclosed in U.S. Pat. No. 6,632,661; which is incorporated herein by reference in its entirety.

The second sheet 22, as illustrated, is coated with layers of adhesive 24 (adhesive 24 preferably and most commonly containing TTC) and powder 26. Adhesive 24 should be coated onto the second sheet 22 in a thickness which does not substantially interfere with or prevent observation (e.g., manual or mechanical observation) of microbial colonies growing in the device and/or does not substantially interfere with or prevent transmission of electromagnetic radiation (e.g., visible light) that is used to observe the microbial colonies. Generally, an adhesive layer in the thickness range of about 5 µm to about 13 µm is suitable.

The powder 26 comprises a dry second cold-water-soluble gelling agent. The second cold-water-soluble gelling agent has properties similar to the first cold-water-soluble gelling agent and may comprise a cold-water-soluble gelling agent that is identical to the first cold-water-soluble gelling agent. The powder 26 is adhered to the second sheet 22 (e.g., adhered to the adhesive 24 which is adhered to the second sheet 22). Powder 26 is coated onto the adhesive 24 as described in U.S. Pat. No. 4,565,783. A uniform monolayer of dry powder 26 is preferred. The powder 26 should have sufficient surface area exposed in a microbial growth zone to act in concert with the dry culture medium 16 absorb a predefined volume of an aqueous liquid deposited in the growth zone during use of the device.

As used in the specification and claims, the term "powder" designates a finely-divided particulate material having an average diameter of less than 400 micrometers. As used in the specification and claims, the term "cold-water-soluble" designates material which forms a solution in water at room temperature.

The microbial growth zone is the region in the device into which the sample is placed during inoculation of the device. The first sheet 12 and second sheet 22 enclose the microbial growth zone, with the culture medium 16 and the powder 26 facing each other in the microbial growth zone. Typically, the microbial growth zone is spaced apart from the edges of the first sheet 12 and the second sheet 22 in order to prevent contamination of the sample and/or prevent leakage of the sample out of the device. After an aqueous liquid (e.g., containing the sample to be tested) is placed into the microbial growth zone, the dry, rehydratable culture medium 16 and the powder 26 in the microbial growth zone are hydrated by the liquid to form a semisolid culture medium for growing coliform bacterial colonies. The microbial growth zone is free of matrixes that prevent visualization of the bacterial colonies.

In any embodiment, the microbial growth zone optionally is defined by a spacer element applied to the surface of first sheet 12 onto which the dry culture medium 16 is coated. The spacer element comprises a piece of spacer 18 having an aperture 20 (e.g., a circular aperture, a square aperture, a rectangular aperture) cut through the center to expose the dry culture medium 16. The walls of aperture 20 provide a well of predetermined size and shape to confine the medium following hydration. Spacer 18 should be thick enough to form a well of the desired volume, e.g., about 1 milliliter, about 2 milliliters, about 3 milliliters, or about 5 milliliters. Closed cell polyethylene foam is one example of a suitable material for spacer 18, but any material which is hydrophobic (non-wetting), inert to microorganisms, and capable of withstanding sterilization may be used. The aperture 20 forms a perimeter of the microbial growth zone in the culture device. Upon receiving the desired (predetermined) volume, the device forms a hydrated culture medium that facilitates growth and enumeration of coliform colonies.

The dry, rehydratable culture medium 16 comprises organonitrogenous nutrients that facilitate growth of coliform microorganisms, an effective amount of at least one agent that selectively inhibits growth of non-coliform microorganisms, and a first cold-water soluble gelling agent.

The organonitrogenous nutrients of the culture medium 16 provide for rapid recovery (e.g., from heat stress, pH stress, water stress) and growth of coliform microorganisms. The organonitrogenous nutrients provide, for example, amino acids and/or oligopeptides and/or vitamins. Non-limiting examples of suitable organonitrogenous nutrients in any embodiment of a device according to the present disclosure include yeast extract, porcine peptones, an enzymatic digest of gelatin, an enzymatic digest of animal peptone, and a combination of any two or more of the foregoing organonitrogenous nutrients.

The culture medium 16 of devices of the present disclosure includes an effective amount of at least one agent that selectively inhibits growth of non-coliform microorganisms. The agent provides a competitive advantage for growth of coliform microorganisms, relative to at least one non-coliform microorganism, in the device of the present disclosure. Such selective agents, which include antibiotics, for example, are well known to a person having ordinary skill in the art. In any embodiment, the agent comprises bile salts, sodium dodecyl sulfate, or a combination of bile salts and sodium dodecyl sulfate. The effective amount is selected so that, when a predetermined volume of aqueous liquid is deposited in the growth zone, the rehydrated culture medium has a concentration of the at least one agent is sufficiently high to selectively inhibits growth of non-coliform microorganisms but not so high that it substantially inhibits growth of coliform microorganisms (i.e., the coliform microorganisms form observable and identifiable colonies within about 24 hours of incubation at a temperature of about 37° C. to about 45° C.).

The culture medium 16 of devices of the present disclosure is cold-water-soluble. The "cold-water-solubility" of the culture medium employed in the devices of the present invention includes a first cold-water-soluble gelling agent in the culture medium. Suitable first cold-water-soluble gelling agents for inclusion in culture medium 16 include both natural and synthetic gelling agents which form solutions in water at room temperature. Gelling agents such as guar gum. polyacrylamide, locust bean gum and agar, for example, form solutions in water at room temperature and are suitable first cold-water-soluble gelling agents for providing a dry, rehydratable culture medium that is "cold-water-soluble" according to the present disclosure. Preferred first cold-water-soluble gelling agents for culture medium 16 include, for example, guar gum and xanthan gum, these gelling agents being useful individually or in combination with one another and in combination with other cold-water-soluble gelling agents. Organonitrogenous nutrients for growing coliform microorganisms form solutions in water at room temperature.

After the culture medium is coated onto the first sheet and dried thereon, the dry culture medium adhered to the first sheet has a coating weight. The coating weight of the dry culture medium is selected so that, when the growth zone is rehydrated with a predefined volume of aqueous liquid (e.g., an aqueous liquid comprising a sample to be tested for coliform and $E.$ $coli$ microorganisms), the rehydrated culture medium has the appropriate concentration of each ingredient to facilitate growth and differential enumeration of coliform and $E.$ $coli$ microorganisms. In any embodiment, the coating weight of the dry culture medium adhered to the first sheet can be about 130 mg/100 cm$^2$ to about 195 mg/100 cm$^2$.

The dry, rehydratable culture medium of a device according to the present disclosure comprises a lactose-fermentation indicator system disposed in the microbial growth zone. The lactose fermentation indicator system provides two indications of colonies of coliform bacteria growing in device: a first indication (acid production) due to the fermentation of lactose and a second indication (gas production) due to the fermentation of lactose. The production of both acid and gas ($CO_2$) from the fermentation of lactose confirm a presence of a colony of coliform microorganisms growing in the device. The presence of acid and gas in combination with the precipitation of the TTC reduction product 'formazan' at the point of colony growth can provide differentiation of coliform bacteria from the inducible and constitutive *E. coli* organisms. Accordingly, the lactose fermentation indicator system comprises D-lactose and a pH indicator. The pH indicator has a transition range around 7.0. Suitable pH indicators include sulfonephthalein pH indicators such as phenol red and chlorophenol red, for example.

The lactose-fermentation indicator system further includes a first inducer compound that enhances production of enzymes (e.g., β-galactosidase) for utilizing lactose. Non-limiting examples of suitable first inducer compounds include isopropyl-β-D-thiogalactoside (IPTG) and phenyl-β-D-galactoside.

The lactose-fermentation indicator system is disposed (e.g., in the dry, rehydratable culture medium) in the microbial growth zone of the culture device. Thus, in any embodiment, at least one of the components of the lactose-fermentation indicator system can be added to the culture medium before the culture medium is coated onto the first sheet 12 and/or the first adhesive 14. Alternatively, at least one component of the lactose-fermentation indicator system can be included in an aqueous liquid (e.g., water, a buffer, and/or the sample) that is deposited into or onto the microbial growth zone when the culture medium is rehydrated for use. In any embodiment wherein the lactose is disposed in the device in the dry culture medium, the lactose is present in the dry culture medium at a coating weight of about 8.5 mg/100 $cm^2$ to about 27 mg/100 $cm^2$.

The dry, rehydratable culture medium of a device according to the present disclosure comprises a β-D-glucuronidase indicator system disposed in the microbial growth zone. The β-D-glucuronidase indicator system provides an indication of colonies, such as *E. coli* colonies, that produce β-D-glucuronidase enzyme activity. Thus, the β-D-glucuronidase indicator system provides a means of distinguishing *E. coli* colonies present in the device from non-*E. coli*-coliform colonies present in the device. Accordingly, the β-D-glucuronidase indicator system comprises a chromogenic β-D-glucuronidase enzyme substrate (e.g., 5-bromo-4-chloro-3-indolyl-β-D-glucuronide). In addition, the β-D-glucuronidase indicator system further comprises a plurality of compounds that enhance β-glucuronidase enzyme activity in *E. coli*. Non-limiting examples of suitable compounds that enhance β-glucuronidase enzyme activity in *E. coli* include methyl-β-D-glucuronide, phenyl-β-D-glucuronide, and D-glucuronic acid. In any embodiment, a first compound that enhances β-glucuronidase enzyme activity in *E. coli* is selected from methyl-β-D-glucuronide and phenyl-β-D-glucuronide. In any embodiment, a second compound that enhances β-glucuronidase enzyme activity in *E. coli* is D-glucuronic acid. Surprisingly, a device having a combination of first and second compounds that enhances β-glucuronidase enzyme activity in *E. coli* is better able to detect β-glucuronidase-positive *E. coli*. Such a combination of compounds for detecting this microorganism type has not been previously known.

Without being bound by theory, it is believed that at least one of the plurality of compounds that enhance β-glucuronidase enzyme activity in *E. coli* may induce the production of more β-glucuronidase enzyme by the cells. Alternatively, or additionally, at least one of the plurality of compounds that enhance β-glucuronidase enzyme activity in *E. coli* may enhance the activity of the β-glucuronidase enzyme molecules when they react with a chromogenic enzyme substrate (e.g., 5-bromo-4-chloro-3-indolyl-β-D-glucuronide).

The β-D-glucuronidase indicator system is disposed (e.g., in the dry, rehydratable culture medium) in the microbial growth zone of the culture device. Thus, in any embodiment, at least one of the components of the β-D-glucuronidase indicator system can be added to the culture medium before the culture medium is coated onto the first sheet 12, the first adhesive 14, or second sheet 22. Alternatively, at least one component of the β-D-glucuronidase indicator system can be included in an aqueous liquid (e.g., water, a buffer, and/or the sample) that is deposited into or onto the microbial growth zone when the culture medium is rehydrated for use.

In any embodiment, a device of the present disclosure can comprise a reagent for buffering the culture medium when the culture medium is reconstituted with an aqueous liquid during use. The reagent can buffer the culture medium (when hydrated during use) at a pH between about 6.5 and 7.5. A non-limiting example of a suitable reagent for buffering the culture medium a phosphate salt (e.g., $Na_2HPO_4$, $NaH_2PO_4$, $K_2HPO_4$, $KH_2PO_4$, or a combination of any two or more of the foregoing reagents). The reagent is disposed (e.g., in the dry, rehydratable culture medium) in the microbial growth zone of the culture device. Thus, in any embodiment, the reagent can be added to the culture medium before the culture medium is coated onto the first sheet 12 and/or the first adhesive 14. Alternatively, the reagent can be included in an aqueous liquid (e.g., water, a buffer, and/or the sample) that is deposited into or onto the microbial growth zone when the culture medium is rehydrated for use.

The components of the culture medium can be mixed together in an aqueous liquid and coated onto the first sheet, for example, as described in Example 12 of U.S. Pat. No. 4,565,783. After coating the culture medium onto the first sheet, the culture medium layer is dried until it is essentially water-free. Optionally, prior to coating the culture medium onto the first sheet, the first sheet is coated with a layer of an adhesive as disclosed herein. Then, the culture medium is coated onto the adhesive layer and dried until the layer of culture medium is essentially water-free.

In any embodiment, it may be desirable to incorporate a non-specific indicator (e.g., a dye) into the microbial growth zone in order to indicate a presence of a microbial colony growing in the device. In some embodiments, the indicator may be incorporated into the culture medium 16. Alternatively, the indicator may be incorporated in adhesive 14. Suitable indicators are those which are metabolized by growing microorganisms, and which cause the colonies to be colored for easier visualization. Examples of such indicators include triphenyl tetrazolium chloride, p-tolyl tetrazolium red, tetrazolium violet, veratryl tetrazolium blue and related dyes.

Optionally, in any embodiment, a device of the present disclosure further comprises powdered infant formula disposed in the microbial growth zone. The infant formula can be provided in the growth zone as a component of the dry culture medium or, alternatively, it can be mixed with the second cold-water-soluble gelling agent adhered to the adhesive layer 24 on the second sheet. The infant formula provides a plurality of nutrients (e.g., proteins, carbohydrates, minerals and vitamins) that may facilitate growth of coliform microorganisms. A non-limiting example of a powdered infant formula suitable for use in a device of the present disclosure is GERBER® GOOD START® Gentle (Stage 1) Infant Formula available from Nestle Infant Nutrition; Florham Park, N.J.

In any embodiment wherein the infant formula is disposed in the device in the dry culture medium, the infant formula is present in the dry culture medium at a coating weight up to about 27 mg/100 cm$^2$. In any embodiment, the infant formula can be present in the dry culture medium at a coating weight up to about 14 mg/100 cm$^2$. In any embodiment, the infant formula can be present in the dry culture medium at a coating weight up to about 19 mg/100 cm$^2$.

Thin film culture devices have been used to grow and enumerate colonies of microorganisms (e.g., species of pathogenic *E. coli*) and the colonies have subsequently been transferred (e.g., "blotted") onto a membrane for identification of the microorganisms, for example, as described in U.S. Pat. No. 5,137,812; which is incorporated herein by reference in its entirety. It is contemplated that, in some embodiments, thin film culture devices according to the present disclosure can also be used to grow and enumerate colonies of microorganisms that are subsequently transferred (e.g., "blotted") onto a membrane for identification of the microorganisms.

In any embodiment, a culture device of the present disclosure can comprise a dry, rehydratable culture medium adhered to the first sheet wherein the dry, rehydratable culture medium comprises the components listed in Table 1.

TABLE 1

List of components of an exemplary dry, rehydratable culture medium of the present disclosure.
Component Yeast Extract
Porcine Peptone
Phenol Red
Bile Salts
Sodium dodecyl sulfate
MgCl$_2$
Lactose
Methyl Glucuronide
D-Glucuronic Acid
BCIG
K$_2$HPO$_4$
KH$_2$PO$_4$
Infant Formula powder
Enzymatic Digest of Gelatin
Enzymatic Digest of Animal Tissue
Ferric Ammonium Citrate
CaCl$_2$
IPTG
Re-extracted guar gum Organonutrigenous compounds: Yeast Extract; Porcine Peptone; Lactose; Enzymatic digests of animal tissue; enzymatic digests of gelatin, infant formula pH indicator; phenol red
Salts: MgCl2, FAC, Bile Salts, KH2PO4; K2HPO4
Inducers: methyl glucuronide; D-glucuronic acid, IPTG
Indicators: BCIglucuronide
Gelling agents: Guar gum In another aspect, the present disclosure provides a method of differentially enumerating colonies of coliform and *Escherichia coli* microorganisms. The method comprises contacting a sample and an aqueous liquid in the microbial growth zone of any embodiment of the culture device of the present disclosure to form an inoculated culture device. In any embodiment, the sample can comprise the aqueous liquid. In general, the amounts of gelling agent; indicator agents (TTC and BCIG); and dry culture medium in microbial growth zone of the culture device are selected to provide an effective concentration for detecting and distinguishing colonies of coliform bacteria and *E. coli* when they (i.e., the gelling agent, indicator agents, and nutrient) are reconstituted with a predetermined volume (e.g., 1 milliliter, 2 milliliters, 5 milliliters) of aqueous liquid. In any embodiment, the aqueous liquid can be added with the sample materials (e.g., the sample material can be dissolved, homogenized, suspended, and/or diluted in an aqueous liquid such as sterile water, an aqueous buffer, or an aqueous nutrient medium, for example). In any embodiment wherein the sample comprises solid (e.g., a membrane filter having retained material thereon or therein) or semisolid materials, the predetermined volume of liquid (e.g., sterile water, an aqueous nutrient medium) can be used to reconstitute the culture device before or after the solid or semisolid sample is used to inoculate the device.

The use of the devices of the present invention will be discussed with specific reference to the device of FIGS. 1 and 2. To use the device of FIGS. 1 and 3 as a pour plate, second sheet 22 is pulled back and a predetermined quantity of water or an aqueous test sample is placed on first sheet 12 in the microbial growth zone defined by the spacer member 18. The components of the dry culture medium 16 adhered to first sheet 12 by adhesive 14 are quickly hydrated or dissolved and a nutrient gel is formed. Second sheet 22 is then replaced over the first sheet, and a weighted plate placed on top to spread the sample completely throughout the microbial growth zone. The device is then incubated for a predetermined period of time.

The sample can be contacted with the microbial growth zone of the culture device using methods that are known in the art (e.g., by pouring or pipetting a liquid sample into the culture device). In any embodiment, the second sheet is typically lifted (e.g., as shown in FIG. 1) to permit deposition of the sample between the first sheet and the second sheet; preferably, into the aperture of a spacer, if present, in the culture device. In any embodiment, contacting a sample and an aqueous liquid with the gelling agent in the microbial growth zone forms an inoculated culture device. After forming the inoculated culture device, the second sheet is lowered to form a protective barrier against contamination and/or excess evaporation of the aqueous liquid during incubation. In any embodiment, the sample may be spread evenly over the microbial growth region, for example by placing a weighted plate on top of the covered device.

In any embodiment, the method further comprises incubating (e.g., in a temperature-controlled environmental chamber) the inoculated culture device for a period of time. The incubation conditions (e.g., the incubation temperature) can affect the rate of growth of coliform bacteria present in the sample. A person having ordinary skill in the art will recognize suitable incubation temperatures to detect coliform bacteria. An inoculated culture device of the present disclosure can be incubated, for example, at temperatures between about 35° C. to about 45° C., inclusive, for example. In any embodiment, the culture device can be incubated in an aerobic (e.g., normal atmospheric) gaseous environment.

The inoculated culture device is incubated for a period of time sufficient to permit the growth of coliform bacteria. The minimum incubation period necessary to detect coliform bacteria is related to the temperature at which the culture device is incubated. For example, in any embodiment wherein the culture device is incubated at about 35°, the period of time can be about 12-hours to about 24 hours, inclusive. In any embodiment wherein the culture device is incubated at about 42°, the period of time can be about 8 hours to about 18 hours, inclusive. In any embodiment wherein the culture device is incubated at about 42°, the period of time can be about 8 hours to about 12 hours, inclusive.

The method of the present disclosure further comprises detecting a colony of coliform bacteria and/or detecting a colony of E. coli bacteria in the culture device (e.g., observing a colony of coliform bacteria and/or detecting a colony of E. coli bacteria in the culture device). In any embodiment, detecting a colony of coliform bacteria in the culture device can comprise detecting in the culture device colonies that have reacted with at least one of the indicator systems (e.g., the lactose-fermentation indicator system and the β-D-glucuronidase indicator system). A colony of coliform bacteria is distinguished by its ability to ferment lactose to acid and gaseous end-products. Thus, detecting a coliform colony comprises observing one or both of reduction of formazan as a precipitate on the colony and an acid zone (as evidence by the pH indicator in the device; e.g., a yellow zone wherein the pH indicator is phenol red) proximate the colony (e.g., within about 1-2 mm of the perimeter of the colony) and also observing a gas bubble trapped in the semisolid culture medium proximate the colony (e.g., either touching the perimeter of the colony or within about 1 mm of the perimeter of the colony).

In addition to observing the acid zone and gas bubble(s) proximate the colony, detecting and distinguishing a colony of E. coli bacteria further comprises detecting a product of β-glucuronidase enzyme activity. For example, when the β-glucuronidase indicator system comprises BCIG, the E. coli colonies will appear blue (or bluish green) with or without a small blue (or bluish) zone surrounding each of the colonies.

In any embodiment, the method of the present disclosure further comprises enumerating colonies of coliform bacteria, if present, and or colonies of E. coli, if present, in the inoculated culture device after incubating the inoculated culture device. Thus, after the colonies of coliform and E. coli bacteria are detected as described herein, the number of detected colonies is determined either manually or using automated processes known in the art (e.g., using an automated colony counter such as, for example, a PETRIFILM Plate Reader available from 3M Company; St. Paul, Minn.).

Exemplary Embodiments

Embodiment A is a device for differentially enumerating colonies of coliform and *Escherichia coli* microorganisms, the device comprising:
   a water-impermeable first sheet;
      a water-impermeable second sheet attached to the first sheet;
      a dry, rehydratable culture medium adhered to the first sheet;
         wherein the culture medium comprises:
            organonitrogenous nutrients that facilitate growth of coliform microorganisms;
            a lactose-fermentation indicator system disposed in the microbial growth zone, the lactose-fermentation indicator system comprising D-lactose, a first inducer compound that enhances production of β-galactosidase, and a pH indicator;
            a β-D-glucuronidase indicator system disposed in the growth zone, the β-D-glucuronidase indicator system comprising 5-bromo-4-chloro-3-indolyl-β-D-glucuronide and a plurality of compounds that enhance β-glucuronidase enzyme activity in E. coli;
            a redox indicator system to enable the differentiation of coliforms from E. coli
            an effective amount of at least one agent that selectively inhibits growth of non-coliform microorganisms; and
            a first cold-water soluble gelling agent;
         a microbial growth zone disposed between the first sheet and the second sheet, wherein an area of the culture medium adhered to the first sheet defines the growth zone; and
         a second cold-water-soluble gelling agent adhered to the second sheet;
      wherein the first sheet is attached to the second sheet so that the culture medium is facing the second cold-water-soluble gelling agent.

Embodiment B is the device of Embodiment A, wherein a first compound of the plurality of compounds that enhance β-glucuronidase enzyme activity in E. coli is selected from methyl-β-D-glucuronide and phenyl-β-D-glucuronide.

Embodiment C is the device of Embodiment A or Embodiment B, wherein a second compound of the plurality of compounds that enhance β-glucuronidase enzyme activity in E. coli is D-glucuronic acid.

Embodiment CC is the device of any one of the preceding embodiments wherein the redox indicators system is tetrazolium chloride.

Embodiment D is the device of any one of the preceding Embodiments, wherein the first sheet and second sheet are configured to retard passage of carbon dioxide therethrough.

Embodiment E is the device of any one of the preceding Embodiments, further comprising D-glucuronic acid disposed in the microbial growth zone.

Embodiment F is the device of any one of the preceding Embodiments, wherein the first sheet comprises a polyester film.

Embodiment G is the device of any one of Embodiments D through F, wherein the second sheet comprises a polyester film.

Embodiment H is the device of Embodiment G, wherein the second sheet comprises polyethylene terephthalate.

Embodiment I is the device of any one of the preceding Embodiments, wherein the growth zone is defined by a spacer adhered to the first sheet.

Embodiment J is the device of any one of the preceding Embodiments, wherein the cold-water soluble gelling agent comprises guar gum.

Embodiment K is the device of any one of the preceding Embodiments, wherein the culture medium adhered to the first sheet has a coating weight of about 130 mg/100 cm$^2$ to about 195 mg/100 cm$^2$.

Embodiment L is the device of any one of the preceding Embodiments, wherein lactose is disposed in the dry culture medium adhered to the first sheet, wherein the lactose is present in the dry culture medium at a coating weight of about 8.5 mg/100 cm$^2$ to about 27 mg/100 cm$^2$.

Embodiment M is the device of any one of the preceding Embodiments, wherein the culture medium further comprises a reagent for buffering the culture medium, when reconstituted with an aqueous liquid, at a pH between about 6.5 and about 8.

Embodiment N is the device of any one of the preceding Embodiments, wherein the pH indicator comprises a sulfonephthalein pH indicator.

Embodiment O is the device of Embodiment N, wherein the pH indicator is selected from a group consisting of chlorophenol red and phenol red.

Embodiment P is the device of any one of the preceding Embodiments, wherein the organonitrogenous nutrients are selected from a group consisting of yeast extract, porcine peptones, an enzymatic digest of gelatin, an enzymatic digest of animal peptone, and a combination of any two or more of the foregoing organonitrogenous nutrients.

Embodiment Q is the device of any one of the preceding Embodiments, wherein the growth zone is configured to receive an aqueous liquid having a predetermined volume of about 1 milliliter to about 5 milliliters and, upon receiving the predetermined volume, forms a hydrated culture medium that facilitates growth and enumeration of coliform colonies.

Embodiment R is the device of any one of the preceding claims, wherein the agent is selected from a group consisting of bile salts, sodium dodecyl sulfate, and combinations thereof.

Embodiment S is the device of any one of the preceding claims, wherein the second cold-water-soluble gelling is disposed on the second film lamina in the form of dry particles or dry agglomerated particles.

Embodiment T is the device of any one of the preceding Embodiments, wherein the first inducer compound that enhances production of β-galactosidase comprises isopropyl-β-D-thiogalactopyranoside.

Embodiment U is the device of any one of the preceding Embodiments, further comprising dry infant formula disposed in the microbial growth zone.

Objects and advantages of this invention are further illustrated by the following examples, but the particular materials and amounts thereof recited in these examples, as well as other conditions and details, should not be construed to unduly limit this invention.

EXAMPLES

Examples 1-13 Fabrication of Microbial Detection Articles

Preparation of Culture Media.

The mixtures shown in Table 1 were prepared in separate containers. The liquid volume of the mixture was brought to 1000 mL with deionized water.

Preparation of First Sheets.

The mixtures shown in Tables 2 and 3 were prepared by first adding the guar gum to the water followed by subsequent addition of remaining components and heated to 80 C to enable pasteurization of the culture medium. After the heating step, the mixture was allowed to cool to ambient temperature and stored at 4° C. until use.

The liquid mixtures were warmed to ambient temperature and coated onto a polyester film and the coated layer was dried as disclosed in Example 1 of U.S. Pat. No. 5,384,766. The dry coating weight of each separate culture medium coated onto individual films was approximately 0.2 to 0.3 g/155 cm$^2$. The coated sheets were cut into 10.2 cm×7.6 cm rectangles.

Polystyrene foam (0.51 mm thick), obtained from American FujiSeal (Shaumberg, Ill.) was used to make spacer elements. On side of the foam sheets was adhered to a release liner coated with adhesive (3M 927 Transfer Adhesive). Circles (approximately 6 cm diameter) were die-cut from the foam sheets. The foam sheets were cut into 10.2 cm×7.6 cm rectangles, with the circular holes approximately centered in the rectangles. The release liners were removed, and the spacer elements were adhered (via the adhesive on the foam sheet) to the dry culture medium-coated sheets such that the culture medium was exposed in the circular opening of the foam sheet.

Preparation of Second Sheets.

Bi-axially oriented polypropylene (BOPP) coated with adhesive (3M 927 Transfer Adhesive) containing 5 times the triphenyl tetrazolium chloride (TTC, Part No. 17779; Sigma Chemical Co.; St. Louis, Mo.) described in Example 11 of U.S. Pat. No. 4,565,783. The adhesive-coated BOPP film was subsequently powder-coated with guar gum as described in Example 11 of U.S. Pat. No. 4,565,783. The second sheets were cut into 10.6 cm×7.6 cm rectangles Assembly of the Culture Devices.

Double stick tape was applied along one of the edges (along the narrower dimension) of the foam spacer on each of the first sheets. A second sheet was superimposed over the first sheet (as shown in FIG. 1) so that the coated surface of the second sheet faced the foam spacer adhered the first sheet and the sheets were pressed together to secure the second sheet to the double stick tape.

TABLE 2

| Culture media. All values in the table are reported in grams. Each mixture was dissolved in a total of 1000 mL deionized water. | | | | | | | | |
|---|---|---|---|---|---|---|---|---|
| Component | Medium 87 | Medium 83 | Medium 84 | Medium 88 | Medium 89 | Medium 72 | Medium 66 | Medium 63 |
| Yeast Extract | 5 | 5 | 10 | 5 | 5 | 10 | 10 | 5 |
| Porcine Peptone | 5 | 5 | 10 | 5 | 5 | 10 | 10 | 5 |
| Phenol Red | 0.75 | 0.75 | 0.75 | 0.75 | 0.75 | 0.75 | 0.75 | 0.75 |
| Bile Salts | 5 | 5 | 5 | 5 | 5 | 5 | 5 | 3 |
| Sodium dodecyl sulfate | 0.1 | 0.1 | 0.15 | 0.1 | 0.1 | 0.05 | 0.05 | 0.05 |
| MgCl$_2$ | 0.5 | 0.5 | 0.5 | 0.5 | 0.5 | 0.45 | 0.45 | 0.45 |
| Lactose | 3 | 5 | 5 | 6 | 10 | 10 | 3.5 | 7.5 |
| Methyl Glucuronide | 0.2 | 0.2 | 0.2 | 0.2 | 0.2 | 0.2 | 0.2 | 0.2 |
| D-Glucuronic Acid | 0.2 | 0.2 | 0.2 | 0.2 | 0.2 | 0.2 | 0.2 | 0.2 |
| BCIG | 0.5 | 0.5 | 0.5 | 0.5 | 0.5 | 0.5 | 0.5 | 0.5 |
| K$_2$HPO$_4$ | 6 | 6 | 6 | 6 | 6 | 6 | 6 | 6 |
| KH$_2$PO$_4$ | 2 | 2 | 2 | 2 | 2 | 2 | 2 | 2 |
| Infant Formula powder | 0 | 0 | 0 | 0 | 0 | 0 | 0 | 5 |

TABLE 2-continued

Culture media. All values in the table are reported in grams. Each mixture was dissolved in a total of 1000 mL deionized water.

| Component | Medium 87 | Medium 83 | Medium 84 | Medium 88 | Medium 89 | Medium 72 | Medium 66 | Medium 63 |
|---|---|---|---|---|---|---|---|---|
| Enzymatic Digest of Gelatin | 1 | 1 | 5 | 2 | 5 | 5 | 5 | 2.5 |
| Enzymatic Digest of Animal Tissue | 1 | 1 | 5 | 2 | 5 | 5 | 5 | 2.5 |
| Ferric Ammonium Citrate | 0.5 | 0.5 | 0.5 | 0.5 | 0.5 | 0.5 | 0.5 | 0.5 |
| $CaCl_2$ | 0.5 | 0.5 | 0.5 | 0.5 | 0.5 | 0.5 | 0.5 | 0.5 |
| IPTG | 0.2 | 0.2 | 0.2 | 0.2 | 0.2 | 0.2 | 0.2 | 0.2 |
| Re-extracted guar gum | 16 | 16 | 16 | 16 | 16 | 16 | 16 | 16 |

TABLE 3

Culture media. All values in the table are reported in grams. Each mixture was dissolved in a total of 1000 mL deionized water.

| Component | Medium 62 | Medium 69 | Medium 64 | Medium 70 |
|---|---|---|---|---|
| Yeast Extract | 10 | 7.5 | 10 | 10 |
| Porcine Peptone | 10 | 7.5 | 10 | 10 |
| Phenol Red | 1 | 0.75 | 0.75 | 0.75 |
| Bile Salts | 5 | 5 | 5 | 5 |
| Sodium dodecyl sulfate | 0.05 | 0.1 | 0.05 | 0.1 |
| $MgCl_2$ | 0.45 | 0.5 | 0.45 | 0.5 |
| Lactose | 7.5 | 7 | 5 | 10 |
| Methyl Glucuronide | 0.2 | 0.2 | 0.2 | 0.2 |
| D-Glucuronic Acid | 0.2 | 0.2 | 0.2 | 0.2 |
| BCIG | 0.5 | 0.5 | 0.5 | 0.5 |
| $K_2HPO_4$ | 6 | 6 | 6 | 6 |
| $KH_2PO_4$ | 2 | 2 | 2 | 2 |
| Infant Formula powder | 5 | 7 | 10 | 10 |
| Enzymatic Digest of Gelatin | 5 | 5 | 5 | 5 |
| Enzymatic Digest of Animal Tissue | 5 | 5 | 5 | 5 |
| Ferric Ammonium Citrate | 0.5 | 0.5 | 0.5 | 0.5 |
| $CaCl_2$ | 0.5 | 0.5 | 0.5 | 0.5 |
| IPTG | 0.2 | 0.2 | 0.2 | 0.2 |
| Re-extracted guar gum | 16 | 16 | 16 | 16 |

Example 1

Devices were made by adhering first sheets coated with Medium 87 to second sheets prepared as described above.

Example 2

Devices were made by adhering first sheets coated with Medium 83 to second sheets prepared as described above.

Example 3

Devices were made by adhering first sheets coated with Medium 84 to second sheets prepared as described above.

Example 4

Devices were made by adhering first sheets coated with Medium 88 to second sheets prepared as described above.

Example 5

Devices were made by adhering first sheets coated with Medium 89 to second sheets prepared as described above.

Example 6

Devices were made by adhering first sheets coated with Medium 72 to second sheets prepared as described above.

Example 7

Devices were made by adhering first sheets coated with Medium 66 to second sheets prepared as described above.

Example 8

Devices were made by adhering first sheets coated with Medium 63 to second sheets prepared as described above.

Example 9

Devices were made by adhering first sheets coated with Medium 62 to second sheets prepared as described above.

Example 10

Devices were made by adhering first sheets coated with Medium 69 to second sheets prepared as described above.

Example 11

Devices were made by adhering first sheets coated with Medium 64 to second sheets prepared as described above.

Example 12

Devices were made by adhering first sheets coated with Medium 70 to second sheets prepared as described above.

Example 13

Use of the Culture Devices to Grow and Enumerate Coliform or *E. coli* Colonies

*E. coli* ATCC 51813 was obtained from Microbiologics (St. Cloud, Minn.) and subsequently isolated and stored as pure culture frozen glycerol stocks. REC1, a natural *E. coli* strain isolated from Mozzarella cheese which exhibited inducible beta glucuronidase behavior, was stored in glycerol until use.

Overnight cultures of *E. coli* ATCC 51813 and *E. coli* REC1 were serially diluted in Butterfield's buffer as needed to provide countable colonies (e.g., 15-150 CFU/mL) on the culture devices. 1 ml of the diluted sample was inoculate onto the prototype plates. Inoculated plates were incubated at two temperatures (35° C. and 42° C.) and the plates were observed at 24±6 hours.

As controls, the diluted cultures were inoculated into 3M™ PETRIFILM™ E. coli/Coliform Count Plates (PFEC) and 3M™ PETRIFILM™ Select E. coli Count Plates (PSEC) (both obtained from 3M Health Care; St. Paul, Minn.) according to the manufacturer's instructions, incubated for 24±2 hours or 48+/−3 hours, and colonies were counted according to the manufacturer's instructions.

After the incubation period, culture devices from Examples 1-12 were observed to detect and enumerate visible colonies that appeared blue (i.e., glucuronidase-positive, indicative of an E. coli colony) surrounded by a yellow-colored acid zone (i.e., lactose-fermenting colony) with one or more adjacent gas bubbles (i.e., lactose-fermenting colony). The colony counts for each of Examples 1-12 were similar to the counts on the control PETRIFILM plate counts In addition, the colonies on each of the plates were qualitatively analyzed for β-glucuronidase activity and lactose fermentation in each of the culture devices. The results are shown in Table 4.

TABLE 4

Observations of β-glucuronidase activity and lactose fermentation.

|  | E. coli REC1 | | E. coli ATCC 51813 | |
| --- | --- | --- | --- | --- |
|  | β-Glucuronidase Reaction | Gas Production | β-Glucuronidase Reaction | Gas Production |
| Example 1 | +++ | +++ | +++ | +++ |
| Example 2 | +++ | +++ | +++ | +++ |
| Example 3 | +++ | +++ | +++ | +++ |
| Example 4 | +++ | +++ | +++ | +++ |
| Example 5 | + | +++ | +++ | +++ |
| Example 6 | + | +++ | +++ | +++ |
| Example 7 | + | +++ | +++ | +++ |
| Example 8 | +++ | +++ | +++ | +++ |
| Example 9 | + | +++ | +++ | +++ |
| Example 10 | + | +++ | +++ | +++ |
| Example 11 | + | +++ | +++ | +++ |
| Example 12 | + | +++ | +++ | +++ |
| Control - PFEC | + | +++ | +++ | +++ |
| Control - PSEC | +++ | +++ | +++ | + |

For β-Glucuronidase reaction: +++ = Blue/Green colony, + = Red/Purple colony, and − = Red colony.
For Gas production: +++ = large gas bubbles adjacent the colonies, − = Very small gas bubbles adjacent the colonies.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

What is claimed is:

1. A device for differentially enumerating colonies of coliform and *Escherichia coli* microorganisms, the device comprising:
   a water-impermeable first sheet;
   a water-impermeable second sheet attached to the first sheet;
   a dry, rehydratable culture medium adhered to the first sheet;
   wherein the culture medium comprises:
      organonitrogenous nutrients that facilitate growth of coliform microorganisms;
      a lactose-fermentation indicator system disposed in the microbial growth zone, the lactose-fermentation indicator system comprising D-lactose, a first inducer compound that enhances production of β-galactosidase, and a pH indicator;
      a β-D-glucuronidase indicator system disposed in the growth zone, the β-D-glucuronidase indicator system comprising 5-bromo-4-chloro-3-indolyl-β-D-glucuronide and a plurality of compounds that enhance β-glucuronidase enzyme activity in *E. coli*;
      a redox indicator;
      an effective amount of at least one agent that selectively inhibits growth of non-coliform microorganisms; and
      a first cold-water soluble gelling agent;
   a microbial growth zone disposed between the first sheet and the second sheet, wherein an area of the culture medium adhered to the first sheet defines the growth zone; and
   a second cold-water-soluble gelling agent adhered to the second sheet;
   wherein the first sheet is attached to the second sheet so that the culture medium is facing the second cold-water-soluble gelling agent; and
   wherein a second compound of the plurality of compounds that enhance β-glucuronidase enzyme activity in *E. coli* is D-glucuronic acid.

2. The device of claim 1, wherein a first compound of the plurality of compounds that enhance β-glucuronidase enzyme activity in *E. coli* is selected from methyl-β-D-glucuronide and phenyl-β-D-glucuronide.

3. The device of claim 1, wherein the redox indicator is TTC.

4. The device of claim 1, wherein the first sheet and second sheet are configured to retard passage of carbon dioxide therethrough.

5. The device of claim 1, wherein the D-glucuronic acid is disposed in the microbial growth zone.

6. The device of claim 1, wherein the first sheet, the second sheet, or both the first and second sheets comprise a polyester film.

7. The device of claim 6, wherein the second sheet comprises polyethylene terephthalate.

8. The device of claim 1, wherein the growth zone is defined by a spacer adhered to the first sheet.

9. The device of claim 1, wherein the cold-water soluble gelling agent comprises guar gum.

10. The device of claim 1, wherein the culture medium adhered to the first sheet has a coating weight of about 130 mg/100 cm$^2$ to about 195 mg/100 cm$^2$.

11. The device of claim 1, wherein lactose is disposed in the dry culture medium adhered to the first sheet, wherein the lactose is present in the dry culture medium at a coating weight of about 8.5 mg/100 cm$^2$ to about 27 mg/100 cm$^2$.

12. The device of claim 1, wherein the culture medium further comprises a reagent for buffering the culture medium, when reconstituted with an aqueous liquid, at a pH between about 6.5 and about 7.5.

13. The device of claim 1, wherein the pH indicator comprises a sulfonephthalein pH indicator.

14. The device of claim 13, wherein the pH indicator is selected from a group consisting of chlorophenol red and phenol red.

15. The device of claim 1, wherein the organonitrogenous nutrients are selected from a group consisting of yeast extract, porcinepeptones, an enzymatic digest of gelatin, an enzymatic digest of animal peptone, and a combination of any two or more of the foregoing organonitrogenous nutrients.

16. The device of claim 1, wherein the growth zone is configured to receive an aqueous liquid having a predetermined volume of about 1 milliliter to about 5 milliliters and, upon receiving the predetermined volume, forms a hydratedculture medium that facilitates growth and enumeration of coliform colonies.

17. The device of claim 1, wherein the agent is selected from a group consisting of bile salts, sodium dodecyl sulfate, and combinations thereof.

18. The device of claim 1, wherein the second cold-water-soluble gelling is disposed on the second sheet in the form of dry particles or dry agglomerated particles.

19. The device of claim 1, wherein the first inducer compound that enhances production of β-galactosidase comprises isopropyl-β-D-thiogalactopyranoside.

20. The device of claim 1, further comprising dry infant formula disposed in the microbial growth zone.

\* \* \* \* \*